US006850056B2

(12) United States Patent
Fujisaki et al.

(10) Patent No.: US 6,850,056 B2
(45) Date of Patent: Feb. 1, 2005

(54) FLAW DETECTION DEVICE FOR STEEL BAR

(75) Inventors: Keisuke Fujisaki, Futtsu (JP); Kazuomi Tomita, Muroran (JP)

(73) Assignee: Nippon Steel Corporation, Tokyo (JP)

( * ) Notice: Subject to any disclaimer, the term of this patent is extended or adjusted under 35 U.S.C. 154(b) by 0 days.

(21) Appl. No.: 10/363,174

(22) PCT Filed: Sep. 5, 2001

(86) PCT No.: PCT/JP01/07707

§ 371 (c)(1),
(2), (4) Date: Mar. 4, 2003

(87) PCT Pub. No.: WO02/21117

PCT Pub. Date: Mar. 14, 2002

(65) Prior Publication Data

US 2003/0178992 A1 Sep. 25, 2003

(30) Foreign Application Priority Data

Sep. 5, 2000 (JP) ........................................ 2000-269148

(51) Int. Cl.$^7$ .......................... G01N 27/90; G01N 27/82
(52) U.S. Cl. ...................................... 324/238; 324/228
(58) Field of Search .......................... 324/220, 228–229, 324/232, 238–243

(56) References Cited

U.S. PATENT DOCUMENTS 4,602,212 A * 7/1986 Hiroshima et al. ......... 324/227
5,311,127 A  5/1994 Bisiaux
6,249,119 B1 * 6/2001 Curtis et al. ................ 324/242

FOREIGN PATENT DOCUMENTS

| JP | 58-102150 | 6/1983 |
| JP | 59-084404 | 5/1984 |
| JP | 62-032355 | 2/1987 |
| JP | 2-024378 | 2/1990 |
| JP | 4-230846 | 8/1992 |

OTHER PUBLICATIONS

Kazuomi Tomita et al., "Multi–channel Karyuu Tanshou Souchi no Kaihatsu", Zairyou to Process, Sep. 1993, vol. 6, No. 5, p. 1235., there is no translation.

* cited by examiner

Primary Examiner—Bot Ledynh
(74) Attorney, Agent, or Firm—Kenyon & Kenyon

(57) ABSTRACT

A flaw detection device for a steel bar enabling inspection of a high temperature steel bar at a high temperature.

A pre-treatment unit 31, detection unit 32, and post-treatment unit 33 are arranged along a running direction of a steel bar 10. The pre-treatment unit and post-treatment unit have the same structure. Direct current coils 312 and 332 are wound around the outside of the sleeves 311 and 331. The steel bar is magnetically saturated by the direct current magnetic field. An eddy current is generated at the surface of the steel bar by an alternating current coil 321 of a detection unit 12. The change in the magnetic field caused by the eddy current is detected by the detection windings 322 and 323. The sleeves are made of nonmagnetic materials, so the strength of the direct current magnetic field becomes flat along the running axis of the steel bar. Even when moving the steel bar at a high speed, the occurrence of noise due to changes in strength of the direct current magnetic field is suppressed.

4 Claims, 5 Drawing Sheets

FLAW DETECTION DEVICE FOR STEEL BAR

1. TECHNICAL FIELD

The present application relates to a flaw detection device for a steel bar for detecting flaws which occur on the surface of the steel bar, more particularly relates to a flaw detection device for a steel bar able to inspect a high temperature steel bar at a high speed.

2. BACKGROUND ART

Steel bars, one type of ferrous metal product, is produced by rolling. At the time of rolling, however, flaws sometimes occur on the surface of the steel bars. Therefore, inspection for the presence of flaws becomes important in the quality inspection process.

To inspect for flaws, frequently the eddy current flaw detection method is used.

FIG. 1 is a perspective view of a flaw detection device for a steel bar used in the past. The device is comprised of a pre-treatment unit 11, a detection unit 12, and a post-treatment unit 13. The steel bar 11 moves from the pre-treatment unit 11 toward the post-treatment unit 13.

The pre-treatment unit 11 and the post-treatment unit 13 have the same configuration and are comprised of sleeves 111 and 131 comprised of tubular magnetic members and direct current coils 112 and 132 wound around their outsides.

These direct current coils 112 and 132 function to magnetically saturate the ferromagnetic steel bar at a temperature lower than a temperature corresponding to the Curie point by a direct current magnetic flux generated by the direct current coils 112 and 132 so as to raise the flaw detection sensitivity when using the substantial alternating current permeability as the zero point.

The detection unit 12 is comprised of a cylindrically shaped direct current coil 121 and two short tubular detection coils 122 and 123 arranged inside it. The two detection coils 122 and 123 are differentially connected in series and for example are connected to a voltmeter as a measuring device (not shown). The alternating current coil 121 functions to generate an eddy current at the surface of the steel bar, while the detection coils 122 and 123 detect disturbances in the magnetic field due to disturbances in the eddy current caused by flaws on the surface of the steel bar.

With the conventional eddy current flaw detection device, however, maintenance of the flaw detection accuracy required that an approximately room temperature steel bar be moved at a speed of about 2 m/sec, so the productivity ended up low. Due to this:

(1) Since a steel bar is about 800° C. in the withdrawal step, it is necessary to provide a cooling time for cooling them to approximately room temperature before entering the quality inspection process.

(2) Since the speed of movement of the steel bar is a slow one of about 2 m/sec, the inspection itself takes time.

If trying to inspect a high temperature steel bar at a high speed by an eddy current flaw detection device used in the past, the following problems arise:

(1) Since the pre-treatment unit 11 and post-treatment unit 13 are separated from each other and the sleeves 112 and 132 for preventing contact of the steel bar with the direct current coils 112 and 132 are made of magnetic materials, if increasing the inspection speed to about 120 m/sec, noise unavoidably occurs due to the changes in axial direction of the magnetic field strength.

FIG. 2 is a view of the distribution of the magnetic field strength in the axial direction of a flaw detection device for a steel bar used in the past. Inside the sleeves 111 and 131, the strength is constant, but at the two ends of the sleeves 111 and 131, the strength sharply changes.

Therefore, when the steel bar passes the two ends of the sleeves 111 and 131 where the magnetic strength changes sharply, current is induced at the surface of the steel bar. If a low speed of about 2 m/sec, the current caused at the detection coils 122 and 123 due to the induction current does not have any effect on the flaw detection, but at a high speed of about 120 m/sec, the current caused at the detection coils 122 and 123 becomes noise and influences the detection accuracy.

Therefore, to make the detection accuracy high, it is important to flatten the distribution of the magnetic strength in the axial direction of the eddy current flaw detection device.

(2) Near room temperature, the relative permeability of a steel bar is substantially constant, so even if the temperature fluctuates somewhat, it is possible to maintain the inspection accuracy.

At 700 to 400° C., however, with a magnetic field able to magnetically saturate a steel bar at room temperature, the relative permeability fluctuates dramatically in accordance with changes in temperature and it is not possible to maintain the inspection accuracy.

Therefore, it becomes important to increase the strength of the direct current magnetic field for magnetically saturating the steel bar and improving the temperature characteristic of the relative permeability.

The present invention was made in consideration of the above problems and has as its object the provision of a flaw detection device for a steel bar enabling inspection of a high temperature steel bar at a high speed.

3. DISCLOSURE OF THE INVENTION

The flaw detection device of steel bars according to the first aspect of the invention comprises a pretreatment unit and post-treatment unit each provided with a cylindrically shaped sleeve and a direct current magnetizing means for magnetizing by a direct current a steel bar running along a center axis of the cylindrically shaped sleeve; a detection unit provided with an eddy current generating means arranged between the pre-treatment unit and post-treatment unit in the running direction of the steel bar for generating an eddy current at the surface of the steel bar and a magnetic field change detecting means for detecting a change in magnetic field caused by an eddy current generated by the eddy current generating means; and a magnetic field strength flattening means for flattening the strength of the magnetic field generated by the direct current magnetizing means along the running direction.

In the present invention, since the strength of the magnetic field generated by the direct current magnetizing means is flattened along the running axis, even when moving the steel bar at a high speed, the generation of noise due to the magnetic field distribution is suppressed and maintenance of a high flaw detection accuracy becomes possible.

In the flaw detection device for a steel bar according to a second aspect of the invention, the direct current magnetizing means generates a magnetic field of a strength imparting to the steel bar a relative permeability characteristic decreasing monotonously with respect to a rise of temperature.

In the present invention, a relative permeability characteristic which decreases monotonously with respect to rises in temperature is imparted to the steel bar, so evaluation of the measurement results becomes easy.

4. BRIEF DESCRIPTION OF THE DRAWINGS

5. BEST MODE FOR CARRYING OUT THE INVENTION

Figure 1:
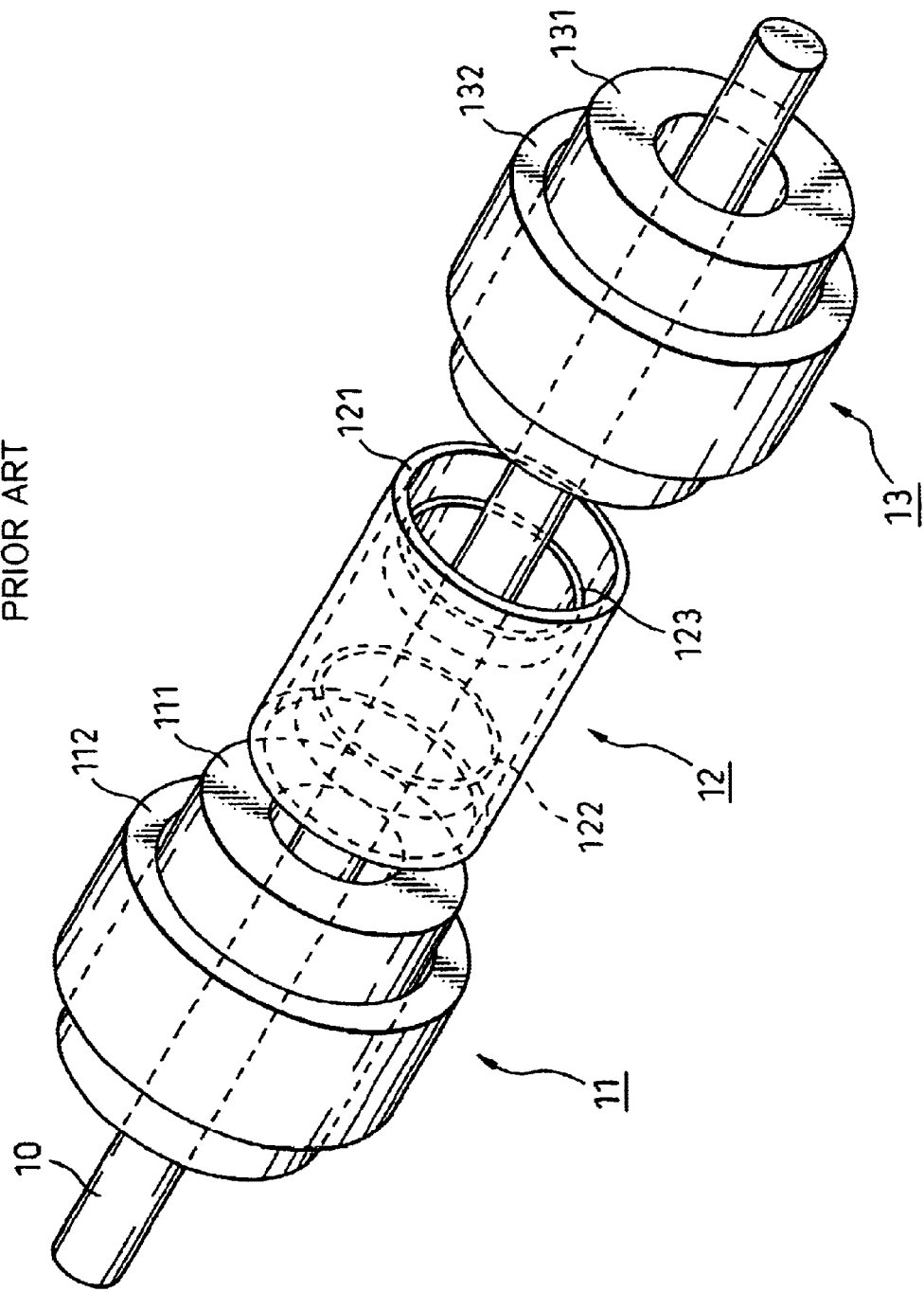
FIG. 1 is a perspective view of a flaw detection device for a steel bar used in the past.
Figure 2:
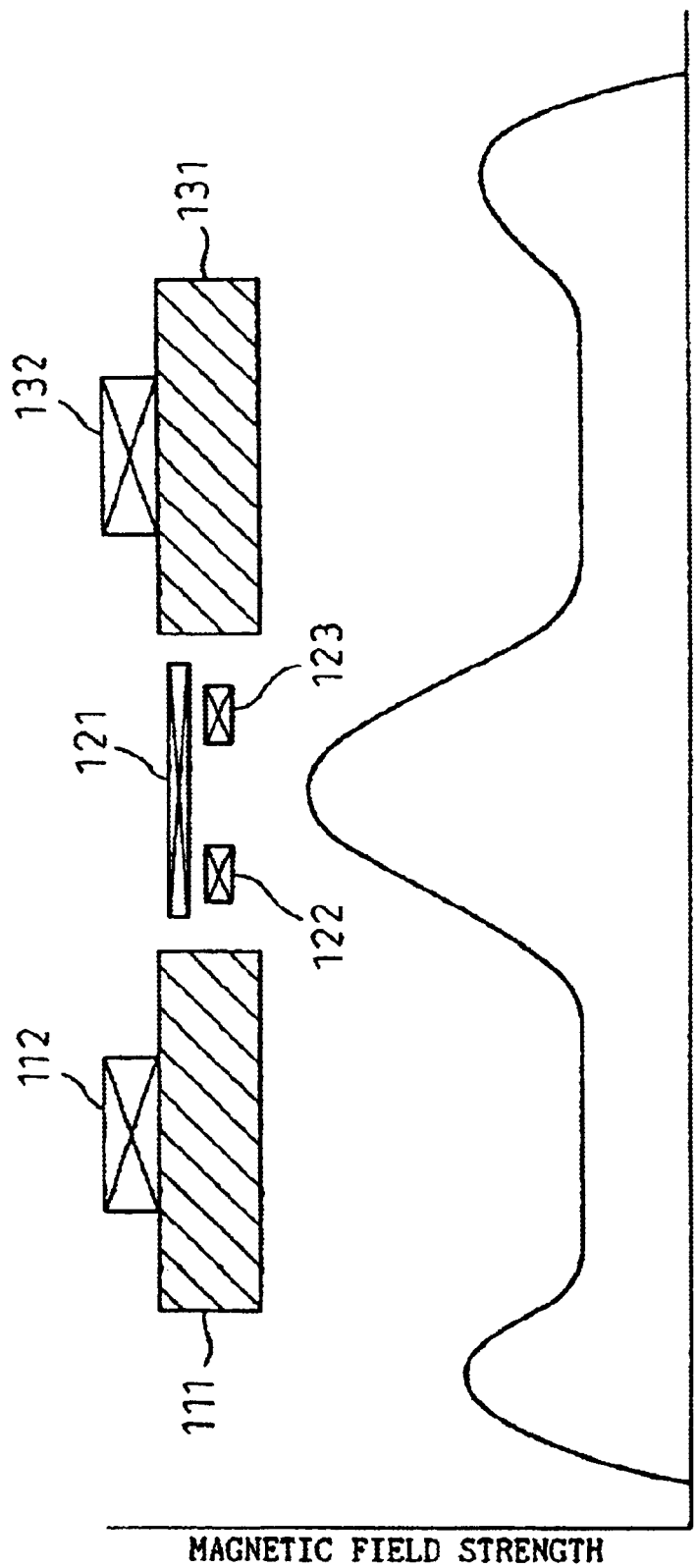
FIG. 2 is a view of the distribution of the magnetic field strength in the axial direction of a flaw detection device for a steel bar used in the past.
Figure 3:
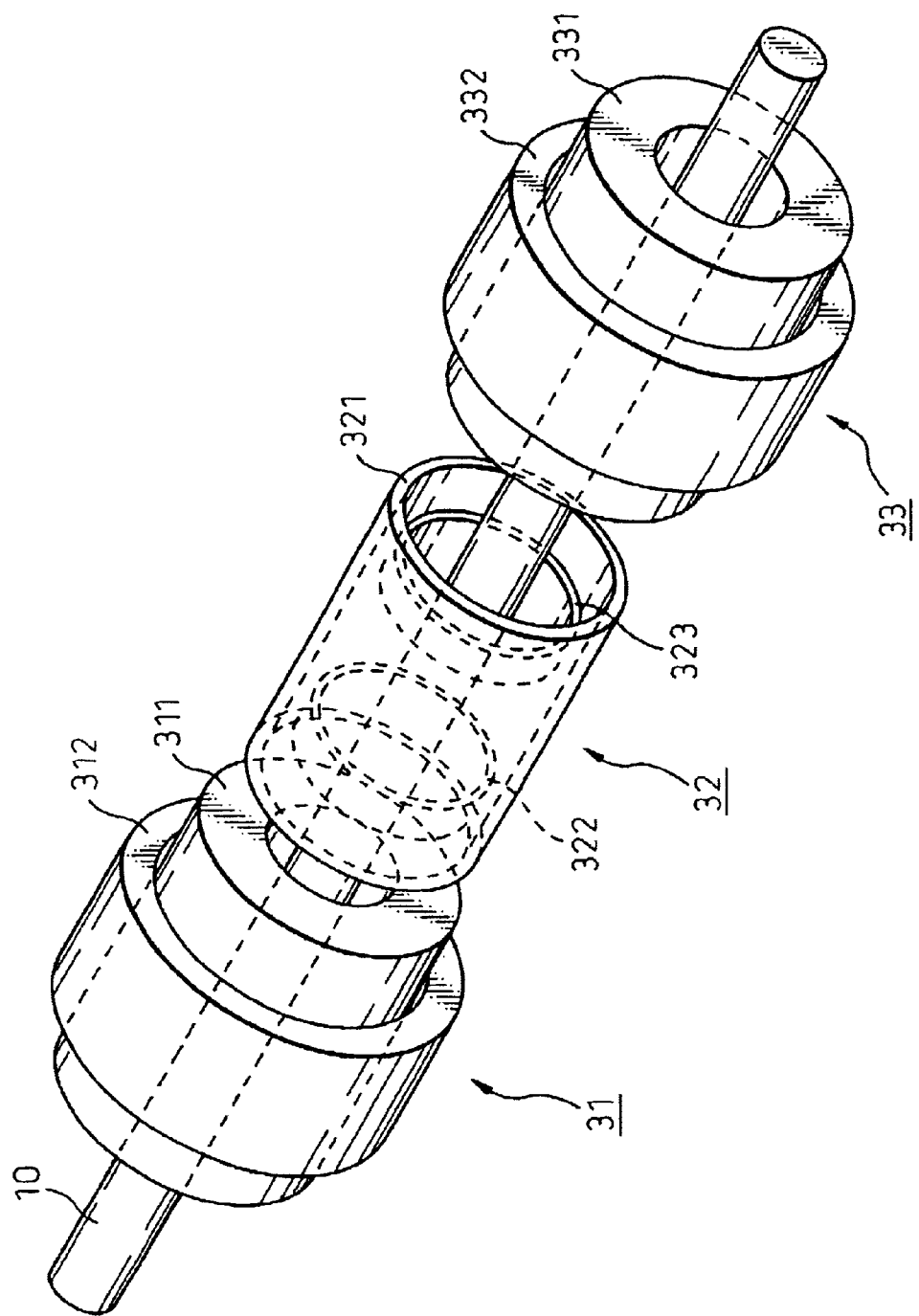
FIG. 3 is a perspective view of a flaw detection device for a steel bar according to a first aspect of the invention.

FIG. 3 is a perspective view of a flaw detection device for a steel bar according to a first aspect of the invention. Flattening of the distribution of the magnetic field strength in the axial direction is realized.

Basically, in the same way as in the past, this is comprised of a pre-treatment unit 31, detection unit 32, and post-treatment unit 33.

The pre-treatment unit 31 and post-treatment unit 33 have the same configuration. They are comprised of tubular sleeves 311 and 331 and direct current coils 312 and 332 wound around their outsides. The direct current coils 312 and 332 are supplied with direct current power from a direct current power source (not shown) and generate a direct current magnetic field in the axial direction.

However, the sleeves 311 and 331 differ from the past in that they are made of a nonmagnetic material. The strength of the direct current magnetic field generated by the direct current coils 312 and 332 does not fall even inside the sleeves 311 and 331. The distribution of the magnetic field strength in the axial direction therefore becomes flat.

Therefore, even when the steel bar is made to move at a high speed, the occurrence of noise due to changes in the magnetic field strength in the axial direction is suppressed.

The detection unit 32 is comprised of a cylindrically shaped alternating current coil 321 and two short tubular detection coils 322 and 323 arranged inside it. The alternating current coil 321 is excited by an alternating current power source (not shown) and generates an eddy current at the surface of the steel bar.

The two detection coils 322 and 323 are differentially connected in series and are connected to for example a voltmeter as a measuring device (not shown). It detects disturbances in the magnetic field occurring due to disturbances in the eddy current caused by flaws on the surface of the steel bar.

That is, in the first aspect of the invention, the sleeves 311 and 331 have to be made a nonmagnetic material, but in actuality the applicable material is limited to nonmagnetic stainless steel. As a nonmagnetic material, wood or plastic may also be considered, but these cannot be used in a high temperature environment.

Nonmagnetic stainless steel, however, is higher in hardness than the steel bar. When a steel bar contacts a sleeve, the surface of the steel bar is liable to be damaged.

Figure 4:
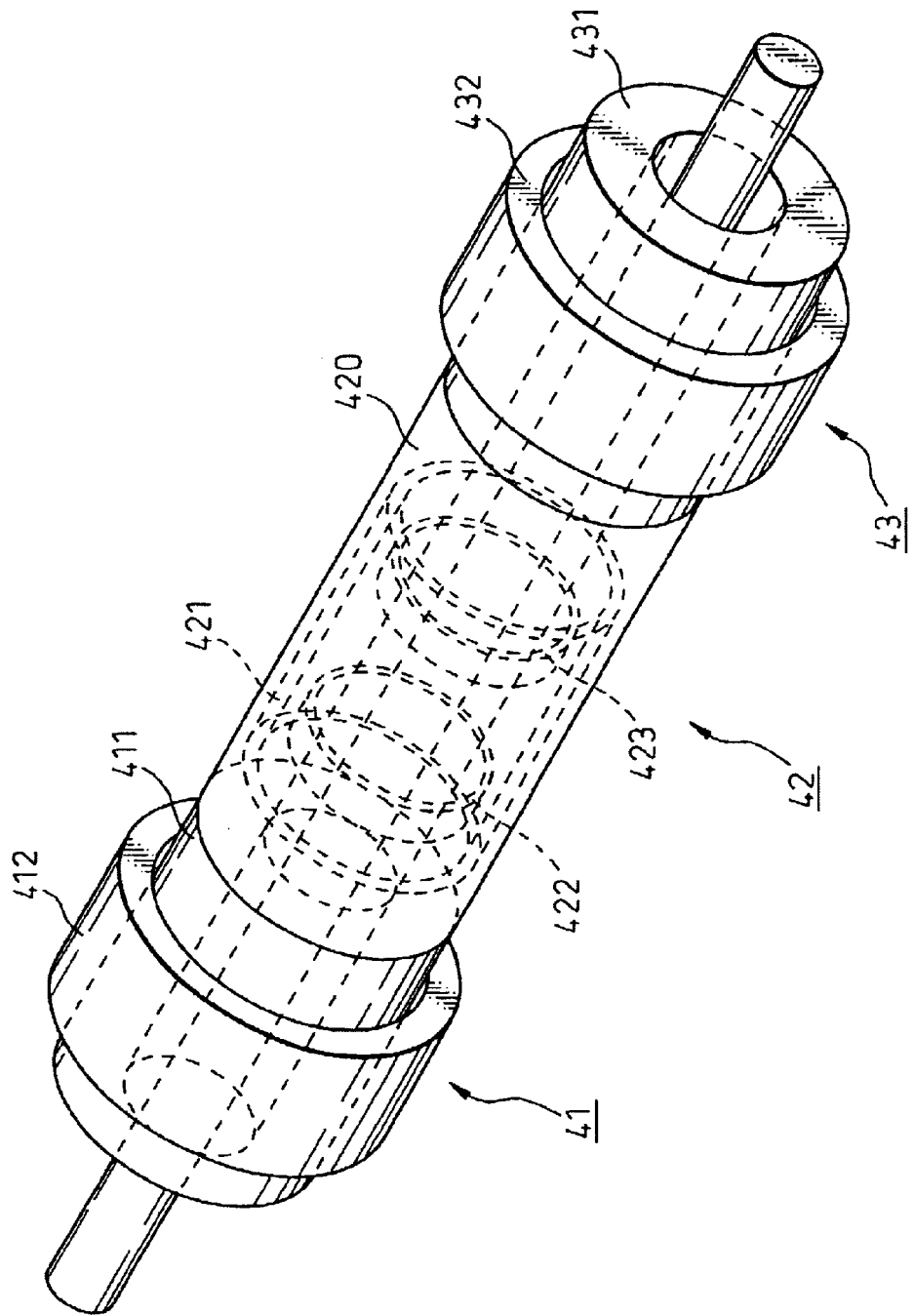
FIG. 4 is a perspective view of a flaw detection device for a steel bar according to a second aspect of the invention.

FIG. 4 is a perspective view of a flaw detection device for a steel bar according to a second aspect of the invention. It is possible to use a magnetic material (for example, a ferrous metal) as the sleeves 411 and 431. Therefore, it is possible to prevent the steel bar from contacting the sleeves and the surface of the steel bar from being damaged.

This aspect of the present invention is also comprised of a pre-treatment unit 41, detection unit 42, and post-treatment unit 43. The pre-treatment unit 41 and post-treatment have the same configurations and are comprised of tubular sleeves 411 and 431 made of a magnetic material (for example, a ferrous metal) and direct current coils 412 and 432 wound around their outsides.

In this aspect of the present invention, to flatten the direct current magnetic field strength, the detection unit 42 is comprised of a cylindrically shaped core 420 having the same outside diameter and inside diameter as the sleeves 411 and 431 and an alternating current coil 421 and two detection coils 422 and 423 wound around it.

Figure 5:
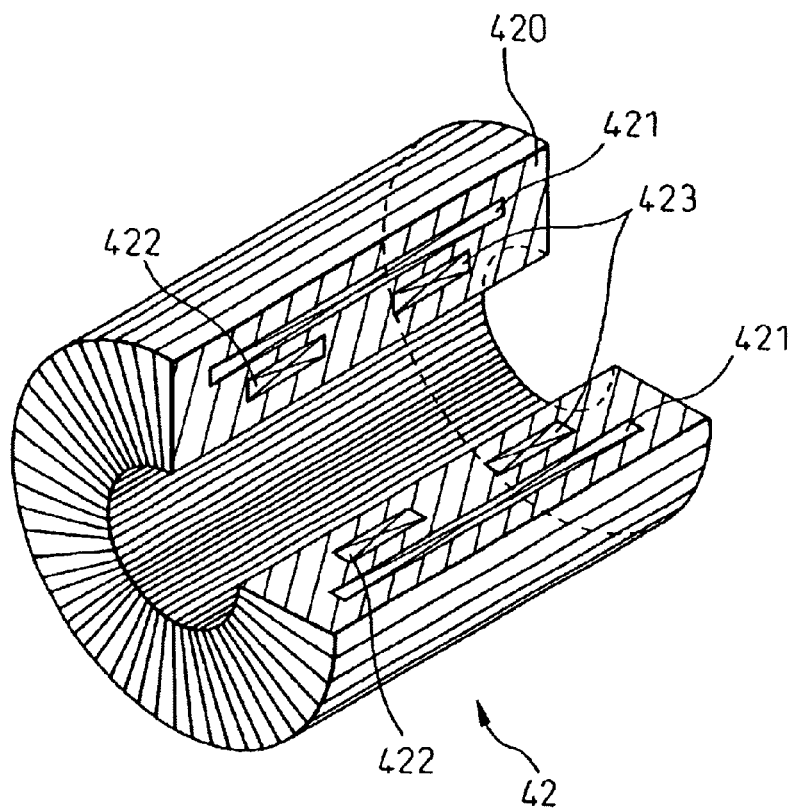
FIG. 5 is a perspective sectional view of a detection unit.

FIG. 5 is a perspective sectional view of the detection unit. To prevent the generation of an eddy current in the core 420, the cylindrically shaped core 420 is configured of thin magnetic steel sheets drawn in the width direction stacked radially.

If making the strength of the magnetic field generated by the direct current coils 412 and 432 the same as that of a conventional eddy current flaw detection device, the detection characteristics of the detection coils 422 and 423 become extremely nonlinear and evaluation of the measurement results becomes difficult.

Figure 6:
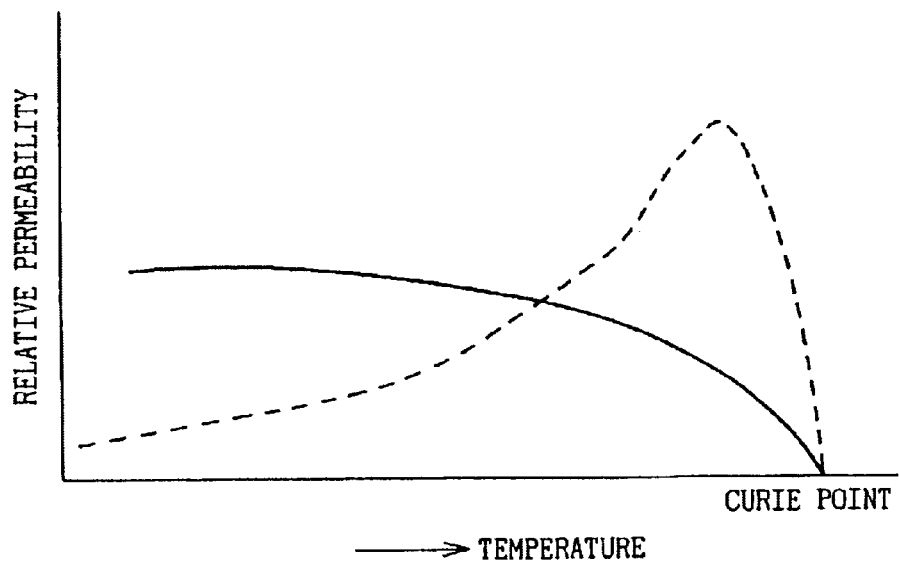
FIG. 6 is a graph of the relative permeability of a steel bar.

FIG. 6 is a graph of the relative permeability of a steel bar. The abscissa indicates the temperature, while the ordinate indicates the relative permeability.

That is, the broken line shows the relative permeability at a conventional direct current magnetic field strength (for example, 70 kA/m). Along with a rise in temperature, the relative permeability becomes larger.

After becoming maximum, it sharply decreases. It becomes zero at the Curie temperature (780° C.). Therefore, when the temperature of the steel bar is in a range of 400 to 700° C., the relative permeability forms a peak in profile. When accurately evaluating the measurement results, it becomes necessary to measure the temperature.

To solve this problem, the strength of the magnetic field generated by the direct current coil 412 and 432 is made approximately double that of the past (for example, 150 kA/m) so that the relative permeability changes monotonously with respect to temperature and the evaluation of the measurement results becomes simplified.

What is claimed is:

1. A flaw detection device for a steel bar provided with:
    a pre-treatment unit and post-treatment unit each provided with a cylindrically shaped sleeve and a direct current magnetizing means for magnetizing by a direct current a steel bar running along a center axis of said cylindrically shaped sleeve;
    a detection unit provided with an eddy current generating means arranged between said pretreatment unit and post-treatment unit in the running direction of said steel bar for generating an eddy current at the surface of said steel bars and a magnetic field change detecting means for detecting a change in magnetic field caused by an eddy current generated by said eddy current generating means; and a magnetic field strength flattening means for flattening the strength of the magnetic field generated by said direct current magnetizing means along the running direction.

2. A flaw detection device for a steel bar as set forth in claim 1, wherein said magnetic field strength flattening means is said sleeves produced by a nonmagnetic material.

3. A flaw detection device for a steel bar as set forth in claim 1, wherein said magnetic field strength flattening means is comprised of:

said sleeves produced by a magnetic material and a stacked core housing said eddy current generating means and said magnetic field change detecting means of said detection unit stacked radially around said running axis.

4. A flaw detection device for a steel bar as set forth in any one of claims 1 to 3, wherein said direct current magnetizing means generates a magnetic field of a strength imparting to the steel bar a relative permeability characteristic decreasing monotonously with respect to a rise of temperature.

* * * * *